US006340696B1

(12) United States Patent
Camden

(10) Patent No.: US 6,340,696 B1
(45) **Date of Patent: *Jan. 22, 2002**

(54) VIRAL TREATMENT

(75) Inventor: James Berger Camden, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/663,578

(22) Filed: Sep. 15, 2000

Related U.S. Application Data

(63) Continuation-in-part of application No. 09/535,173, filed on Mar. 27, 2000, now Pat. No. 6,245,788, which is a continuation-in-part of application No. 09/281,895, filed on Mar. 31, 1999, now abandoned.

(51) Int. Cl.[7] .................... A61K 31/41; A61K 31/7056; A61K 38/21

(52) U.S. Cl. .............................. 514/361; 514/8; 514/25

(58) Field of Search ............................... 514/361, 25, 8

(56) References Cited

U.S. PATENT DOCUMENTS

| | | | | |
|---|---|---|---|---|
| 4,353,920 A | 10/1982 | Gay et al. | | 424/270 |
| 4,835,168 A | 3/1989 | Paget, Jr. et al. | | 514/363 |
| 5,376,670 A | 12/1994 | Conner et al. | | 514/383 |
| 5,593,993 A | 1/1997 | Morin, Jr. et al. | | 514/247 |

FOREIGN PATENT DOCUMENTS

| | | | |
|---|---|---|---|
| EP | 540 143 A2 | | 5/1993 |
| EP | 0540143 | * | 5/1993 |
| WO | WO 99/45027 | | 9/1999 |

OTHER PUBLICATIONS

Kurzer, et al., *J. Chem. Soc. Perkin Trans.,* 1985, vol. 1(2), pp. 311–314 (published by Royal Society of Chemistry).

Kurzer, et al., *J. Heterocyclic Chem.,* 1989, vol. 26(2), pp. 355–360 (published by Hetero Corporation).

Chemical Abstracts 123:339794, Khare et al., 1995, "Synthesis and fungicidal activity of some 5–methylene–2–[5'–aryl–1',3',4'–oxa(thia)diazol–2'–yl] amino–4–thiazolones" (published by American Chemical Society).

Shoeb et al., "Studies in Possible Oral Hypoglycemic Agents, Part III. Synthesis of Some 3–Amino–5–Phenyl and 5–Amino–3–Methyl–1,2,4–Thiadiazole Derivatives", J. Indian Chemical Soc., vol. 40, No. 5, 1963, pp. 369–372, XP000957483 (published by Indian Chemical Society).

Khare, et al., 1995, "Synthesis and fungicidal activity of some 5–methylene–2–[5'–aryl–1',3',4'–oxa(thia)diazol–2'–yl]amino–4–thiazolones", Indian Journal of Chemistry, vol. 34b, pp. 828–831, 1995, published by Scientific Publishers.

Newton, et al., "Cyclic Meso–ionic Compounds. Part 23. Novel Chemistry of 1,2,4–Thiadiazoles and Their Transformation into Meso–ionic 1,2,4–Thiadiazolium Derivatives", J. Chem. Soc. Perkin Trans. I, pp. 75–84, 1984, published by The Royal Society of Chemistry.

* cited by examiner

*Primary Examiner*—Phyllis G. Spivack
(74) *Attorney, Agent, or Firm*—Rose Ann Dabek; Steven W. Miller

(57) ABSTRACT

A pharmaceutical composition that inhibits or slows the growth of viruses in animals, particularly in mammals, while reducing cytoxicity of ribavirin or interferon is disclosed. This same composition can be used to treat viral infections, particularly hepatitis C. The composition preferably comprises from about 10 mg to about 6000 mg of a (5-aryl-1,2,4-thiadiazol)-3-yl thiourea derivative or (5-aryl-1,2,4-thiadiazol)-3-yl urea derivative of the formula:

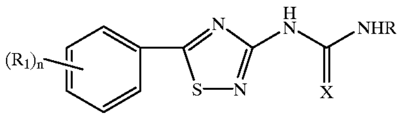

wherein X is oxygen or sulfur, R is hydrogen or alkyl having from 1–3 carbons, n is 0–4, $R_1$ is independently selected from the group consisting of hydrogen, alkyl having from 1 to 7 carbon atoms, chloro, bromo or fluoro, oxychloro, alkoxy having the formula $—O(CH_2)_yCH_3$, wherein y is from 1 to 6, or a pharmaceutically acceptable acid addition salt or prodrug thereof and a safe and effective amount of ribavirin, interferon or mixtures thereof. The preferred compound is (5-phenyl-1,2,4-thiadazol-3-yl) thiourea.

24 Claims, No Drawings

VIRAL TREATMENT

This application is a continuation-in-part of application Ser. No. 09/535,173, filed in the name of James Berger Camden on Mar. 27, 2000, now U.S. Pat. No. 6,245,788, which is a continuation-in-part of Ser. No. 09/281,895 filed Mar. 31, 1999, now abandoned.

TECHNICAL FIELD

This invention is a pharmaceutical composition that is effective in the treatment of hepatitis. The composition can be used to treat viral infections, notably hepatitis, including hepatitis C virus (HCV) and hepatitis B virus (HBV). The composition comprises one or more (5-aryl-1,2,4-thiadiazol)-3-yl-urea or (5-aryl-1,2,4-thiadiazol)-3-yl thiourea derivatives in combination with interferon and/or ribavirin. Methods of treating viral infections are also disclosed.

BACKGROUND OF THE INVENTION

HIV and other viral infections such as hepatitis are a leading cause of death.

Hepatitis is a disease of the human liver. It is manifested with inflammation of the liver and is usually caused by viral infections and sometimes from toxic agents. Hepatitis may progress to liver cirrhosis, liver cancer, and eventually death. Several viruses such as hepatitis A, B, C, D, E and G are known to cause various types of viral hepatitis. Among them, HBV and HCV are the most serious. HBV is a DNA virus with avirion size of 42 nm. HCV is a RNA virus with a virion size of 30–60 nm. See D. S. Chen, J. Formos. Med. Assoc., 95(1), 6–12 (1996).

Hepatitis C infects 4 to 5 times the number of people infected with HIV. Hepatitis C is difficult to treat and it is estimated that there are 500 million people infected with it worldwide (about 15 time those infected with HIV). No effective immunization is currently available, and hepatitis C (HCV) can only be controlled by other preventive measures such as improvement in hygiene and sanitary conditions and interrupting the route of transmission. At present, the only acceptable treatment for chronic hepatitis C is interferon which requires at least six (6) months of treatment. Interferon can inhibit viral replication in infected cells and also improve liver function in some people. Treatment with interferon however has limited long term efficacy with a response rate about 25%.

Hepatitis B virus (HBV) infection can lead to a wide spectrum of liver injury. Moreover, chronic hepatitis B infection has been linked to the subsequent development of hepatocellular carcinoma, a major cause of death. Current prevention of HBV infection is a hepatitis B vaccination which is safe and effective. However, vaccination is not effective in treating those already infected (i.e., carriers and patients). Many drugs have been used in treating chronic hepatitis B and none have been proven to be effective, except interferon.

Treatment of HCV and HBV with interferon has limited success and has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Because the interferon therapy has limited efficacy and frequent adverse effects, a more effective regimen is needed.

In the present invention it has been discovered that the combination of (5-aryl-1,2,4-thiadiazol)-3-yl-urea or (5-aryl-1,2,4-thiadiazol)-3-yl thiourea derivative in combination with interferon works synergistically for the treatment of hepatitis C virus, hepatitis B virus, and other hepatitis infections. Moreover, these same (5-aryl-1,2,4-thiadiazol)-3-yl-urea or (5-aryl-1,2,4-thiadiazol)-3-yl thiourea reduce the level of toxicity of ribavirin, another drug used in the treatment of hepatitis, particularly hepatitis C.

SUMMARY OF THE INVENTION

A pharmaceutical composition for administering, to animals, and in particular warm-blooded animals and humans, infected with a hepatitis virus is disclosed. The composition comprises a therapeutically effective amount of interferon or ribavirin or a combination of interferon and ribavirin with an anti-viral compound selected from the group consisting of a (5-aryl-1,2,4-thiadiazol)-3-yl thiourea derivative or a (5-aryl-1,2,4-thiadiazoly)-3-yl urea derivative having the formula:

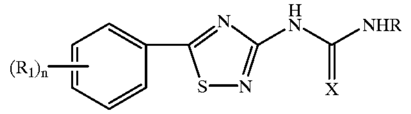

wherein X is oxygen or sulfur; R is hydrogen or alkyl having from 1–3 carbons; n is 0–4; and $R_1$ is independently selected from the group consisting of hydrogen, alkyl having from 1 to 7 carbon atoms, chloro, bromo, fluoro, oxychloro, and alkoxy having the formula $—O(CH_2)_yCH_3$ wherein y is from 1 to 6; or a pharmaceutical addition salt or a prodrug thereof, and optionally a pharmaceutical carrier.

Preferred anti-viral compositions comprise a therapeutically effective amount of the anti-viral compound (5-phenyl-1,2,4-thiadiazoly)-3-yl thiourea, which has the formula:

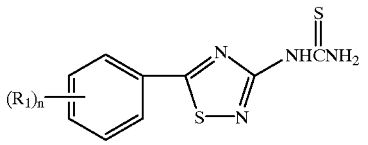

The compositions can be used to treat hepatitis C, hepatitis B, herpes simplex and other viral infections.

More specifically, this invention provides an anti-viral composition comprising a pharmaceutical carrier, interferon or ribavirin or a combination of interferon and ribavirin and a (5-aryl-1,2,4-thiadiazol)-3-yl thiourea derivative or (5-phenyl-1,2,4-thiadiazol)-3-yl urea derivative as defined herein along with a method for treating viral infections for example, hepatitis C, hepatitis B, or other hepatitis infections. The preferred interferon is interferon-alpha.

The compositions can be used in conjunction with other treatments. The route of administration is the same as for other medical treatments. The drug can be given daily or from 1 to 4 times a week.

DETAILED DESCRIPTION OF THE INVENTION

A. DEFINITIONS

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention.

As used herein, the term "therapeutically effective amount" is meant an amount of a compound of the present invention effective to yield the desired therapeutic response. For example an amount effective to treat hepatitis. The specific therapeutically effective amount will, obviously, vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical addition salt" is a salt of the arylthiazolyl thiourea or urea which are modified by making an acid or base salt of the compounds. Examples of pharmaceutical addition salts include, but are not limited to, mineral or organic acid salt of basic residues such as amines, alkali or organic salt of acidic residues such as carboxylic acids. Preferably the salts are made using an organic or inorganic acid. These preferred acid addition salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle for delivering the anti-viral agent to the animal or human. The carrier can be liquid or solid and is selected with the planned manner of administration in mind.

As used herein, the terms "anti-viral compounds" are the (5-aryl-1,2,4-thiadiazol)-3-yl thiourea derivatives or (5-aryl-1,2,4-thiadiazol)-3-yl urea derivative and the pharmaceutical addition salts or prodrugs thereof. The preferred anti-viral compound is 5-phenyl-3-thioureido-1,2,4-thiadiazole.

As used herein, the term "(5-aryl-1,2,4-thiadiazol)-3-yl thiourea derivatives or "(5-aryl-1,2,4-thiadiazol)-3-yl urea derivatives" or "aryl thiadiazolyl thiourea or urea derivatives" includes compounds having the formula:

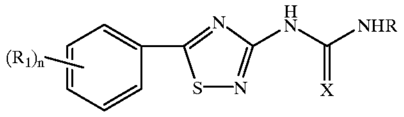

wherein X is oxygen or sulfur, R is hydrogen or alkyl having from 1–3 carbons, n is 0–4, $R_1$ is independently selected from the group consisting of hydrogen, alkyl having from 1 to 7 carbon atoms, chloro, bromo or fluoro, oxychloro, alkoxy having the formula —$O(CH_2)_yCH_3$ wherein y is from 1 to 6 or its pharmaceutical addition salt or its prodrug.

As used herein, "Alkyl" can be any branched, straight chain or cyclic alkane or alkene generally having less than 8 carbons As used herein "Aryl" is any substituted phenyl compound and including phenyl itself wherein R is hydrogen and n is 5.

As used herein, the term "Prodrugs" are any covalently bonded carriers which release the active parent drug according to the formula of derivatives described above in vivo when such prodrug is administered to a mammalian subject or patient in need of treatment. Prodrugs of the arylthiadiazolyl thiourea or urea derivatives arc prepared by modifying functional groups present in the compounds in such a way that the modifications are cleaved, either in routine manipulation or in vivo, to the parent compounds. Prodrugs include compounds wherein free hydroxyl, sulfhydryl, or amine groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the arylthiazolyl thiourea derivatives or arylthiazoloyl urea derivative; phosphate esters, dimethylglycine esters, aminoalkylbenzyl esters, aminoalkyl esters and carboxyalkyl esters of alcohol and phenol functional groups or aminoalkylbenzyl amides, aminoalkyl amides and carboxyalkyl amides of the amino functional groups in the arylthiazolyl thiourea derivatives or arylthiazoloyl urea derivative; and the like.

As used herein "viruses" includes viruses which infect animals or mammals, including humans. Viruses include hepatitis B, hepatitis C and other viral strains of hepatitis, and the like.

As used herein "combination therapy" means that the patient in need of the drug is treated or given another drug for the disease in conjunction with the arylthiazolyl thiourea or arylthiazolyl urea derivatives and interferon or ribavirin or a combination of interferon and ribavirin. This combination therapy can be sequential therapy where the patient is treated first with one or more drugs and then the other, or two or more drugs are given simultaneously.

B. THE (5-ARYL-1,2,4-THIADIAZOL)-3-YL THIOUREA DERIVATIVE OR (5-ARYL-1,2,4-THIADIAZOL)-3-YL UREA DERIVATIVE

The anti-viral material is (5-aryl-1,2,4-thiadiazol)-3-yl thiourea derivative or (5-aryl-1,2,4-thiadiazol)-3-yl urea derivative or their pharmaceutical addition salt or prodrugs having the formula:

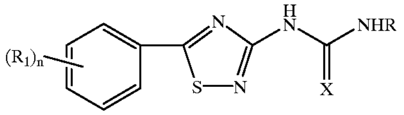

wherein X is oxygen or sulfur, R is hydrogen or alkyl having from 1–3 carbons, n is 0–4, $R_1$ is independently selected from the group consisting of hydrogen, alkyl having from 1 to 7 carbon atoms, chloro, bromo or fluoro, oxychloro, alkoxy having the formula —$O(CH_2)_yCH_3$ wherein y is from 0 to 6, preferably from 2 to 4. Preferably the (5-aryl-1,2,4-thiadiazol)-3-yl-urea or (5-aryl-1,2,4-thiadiazol)-3-yl-thiourea derivative is substituted with an alkyl of less than 4 carbons, a halogen, preferably a chloro in the 7 or 8 position and the remaining substituents of the benzene ring are hydrogen. The most preferred anti-viral is (5-phenyl-1,2,4-thiadiazol)-3-yl thiourea.

Pharmaceutical addition salts of the arylthiazolyl thiourea or arylthiazolyl urea derivatives include the conventional non-toxic salt or the quaternary ammonium salt of the arylthiazolyl thiourea or arylthiazolyl urea derivatives formed, for example, from non-toxic inorganic or organic acids. For example, such conventional non-toxic salt includes those derived from inorganic acids such as hydrochloric, hydrobromic, sulfuric, sulfamic, phosphoric, nitric and the like; and the salt prepared from organic acids such as acetic, propionic, succinic, glycolic, stearic, lactic, malic, tartaric, citric, ascorbic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

SYNTHESIS

The arylthiazolyl thiourea or arylthiazolyl urea derivatives can be prepared in a number of ways well known to one skilled in the art of organic synthesis. The arylthiazolyl thiourea or arylthiazolyl urea derivatives can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference.

The compounds can be synthesized by a desulphurization of aromatic thioureas or urea compounds using hydrogen peroxide in alkali or by reacting the corresponding 3-amino-5-aryl-1,2,4-thiadiazole with ethoxy carbonyl isothiocyanate to produce the ethoxycarbonyl-3-(5'-aryl-1',2',4-thiadiazol-3-yl)thiourea or 3-(5'-aryl-1',2',4'-thiadiazol-3-yl) urea which is then reacted with sodium hydroxide in ethanol and then acidified.

(5-Phenyl-1,2,4-thiadizol)-3-yl thiourea is prepared by the method described in Kurzer, et al, *J. Chem. Soc. Perkin Trans.* 1(2), 311–314 (1985) and Kurzer, et al., *J. Heterocycl. Chem.*, 26 (2), 355–60 (1989).

(5-Phenyl-1,2,4-thiadizol)-3-yl thiourea can also be prepared by the hydrolysis of 3-[N-benzoylthioureido]-5-phenyl-1,2,4-thiadiazole using 3 molar potassium hydroxide at about 60° C. The mixture is cooled, and then acidified with concentrated hydrochloric acid. Concentrated ammonium hydroxide is then used to basify the resultant product. The material from this hydrolysis procedure is pure (about 99%) and the yield is high.

The pharmaceutical addition salt of the present invention can be synthesized from the arylthiazolyl thiourea or arylthiazolyl urea derivatives which contain a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference. The disclosures of all of the references cited herein are hereby incorporated herein by reference in their entirety.

C. INTERFERON AND RIBAVIRIN

These drugs are well known and available commercially. Interferon is available from Amgen (CA) and Research Diagnostic Flanders, N.J.

As used herein, "interferon" refers to one or more interferon materials. The preferred interferon is interferon-alpha. Interferon is a family of species specific vertebrate proteins that confer non-specific resistance to a broad range of viral infections, affect cell production and modulate immune responses. There are three major interferons, alpha, beta and gamma. Other interferon are also known.

Ribavirin nucleaside is available from Schering Plough. The chemical name for ribavirin is 1-β-D-ribofuranosyl-1H-1,2,4-triazole-3carboxamide. It is also known as viramid, virazid and virazole. The combination of ribavirin and interferon is sold under the name Rebetron.

D. DOSAGE

The compounds can be administered in one dose, continuously or intermittently throughout the course of treatment. Methods of determining the most effective means and dosage of administration are well known to those of skill in the art. The compounds may also be given daily or from 1 to 4 times a week. The compounds of the present invention can be given in one or more doses on a daily basis or from one to three times a week. Twice weekly dosing over a period of at least several weeks is preferred. Often the anti-viral compounds will be administered for extended periods of time and may be administered for the lifetime of the patient. Methods of determining the most effective means and dosage of administration are well known to those of skill in the art. Single or multiple administrations can be carried out with one dose level and pattern being selected by the administrator.

The compounds arc generally safe. The oral $LD_{50}$ of (5-phenyl-1,2,4-thiadiazol)-3-yl thiourea is greater than 6000 mg/kg in mice and there are no special handling requirements. By way of general guidance, a dosage of as little as about 1 milligrams (mg) per kilogram (kg) of body weight and preferably as little as 10 mg/kg and up to about 10,000 mg per kg of body weight is suitable for the thiadiazolyl urea or thiourea compounds. Preferably from 10 mg/kg to about 5000 mg/kg of body weight is used. Most preferably the doses are between 250 mg/kg to about 5000 mg/kg. Generally, the dosage in man is lower than for small warm blooded mammals such as mice. By way of guidance the human dose is about 1/12 that of mice. Thus, if 25 mg/kg is effective in mice, a dose of 2 mg/kg would be used for a 60 kg person, and a typical dosage would be 120 mg.

Ribavirin is generally available in a dose of 600 mg to 1200 mg, preferably from 800 mg to 1000 mg. Interferon is generally prescribed in MU (million units) based on its activity. A dose of 9 mg/0.3 ml or 15 mg/0.5 ml provides dose of 3 to 8 MU.

The dosage administered will, of course, vary depending upon known factors, such as the pharmacodynamic characteristics of the particular agent and its mode and route of administration; the age, health and/or weight of the recipient; the nature and extent of the symptoms; the kind of concurrent treatment; the frequency of treatment; and the effect desired.

E. METHOD OF ADMINISTERING AND DOSAGE DELIVERY FORMS

The compounds of the present invention can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into or around the virus.

The dosage amounts are based on the effective inhibitory concentrations observed in anti-viral studies. The preferred route will vary with the (1) condition and age of the recipient, (2) virus and being treated (3) nature of the infection and (4) desired blood levels. It is believed that parenteral treatment by intravenous, subcutaneous, or intramuscular application of the compounds of the present invention formulated with an appropriate carrier, other antiviral agents or compounds or diluents to facilitate application will be the preferred method of administering the compounds to warm blooded animals.

The (5-aryl-1,2,4-thiadizol)-3-yl thiourea derivatives or (5-aryl-1,2,4-thiadizol)-3-yl urea derivatives are preferably micronized or powdered so that it is more easily dispersed and solubilized by the body. Processes for grinding or pulverizing drugs are well known in the art. For example, a hammer mill or similar milling device can be used. The preferred particle size is less than about 100$\mu$ and preferably less than 50μ. These compounds are not very soluble, and therefore are preferably given in tablet form or as a suspension. Suitable methods of administering the compounds of the present invention and dosage forms can be found herein below.

The (5-aryl-1,2,4-thiadizol)-3-yl thiourea derivatives or (5-aryl-1,2,4-thiadizol)-3-yl urea derivatives of this invention can be administered as treatment for viral infections by any means that produces contact of the active agent with the agent's site of action in the body. They can be administered by any conventional means available for use in conjunction with pharmaceuticals, either as individual therapeutic agents or in a combination of therapeutic. Preferably the compounds of the present invention are administered as a pharmaceutical formulation comprising at least one compound of the present invention, as defined above, together with one or more pharmaceutically acceptable carriers. It can be co-administered in the form of a tablet or capsule, as an agglomerated powder or in a liquid form or as a liposome.

These compounds may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

The (5-aryl-1,2,4-thiadiazol)-3-yl thiourea derivatives or (5-aryl-1,2,4-thiadiazol)-3-yl urea derivatives of the present invention can also be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

1. Combination Therapy

The (5-aryl-1,2,4-thiadiazol)-3-yl thiorurea derivatives or corresponding urea derivatives can additionally be combined with other antiviral compounds to provide the operative combination in addition to the interferon and ribavirin. It is intended to include any chemically compatible combination of a compound of this inventive group with other compounds of the inventive group or other compounds outside of the inventive group, as long as the combination does not eliminate the antiviral activity of the compound of this inventive group. For example, one or more (5-aryl-1,2,4-thiadiazol)-3-yl thiourea derivatives or (5-aryl-1,2,4-thiadizol)-3-yl urea derivatives can be combined with other antiviral agents or potentiators. Potentiators are materials which affect the body's response to the anti-viral agent.

In the case of hepatitis, cyclovir, famciclovir or valacyclovir, ribavirin, interferon or combinations of ribavirin and interferon or beta globulin can be administered as a combination therapy.

A "potentiator" can be any material which improves or increases the efficacy of the pharmaceutical composition or acts as an immunomodulator. One such potentiator is triprolidine and its cis-isomer which is used in combination with more (5-aryl-1,2,4-thiadiazol)-3-yl thiourea derivatives or (5-aryl-1,2,4-thiadizol)-3-yl urea derivatives and optionally another therapeutic agent and or anti-viral agent. Triprolidine is described in U.S. Pat. No. 5,114,951 (1992). Another potentiator is procodazole, 1H-benzimidazole-2-propionic acid; [β-(2-benzimidazole) propionic acid; 2-(2-carboxyethyl)benzimidazole; propazol]. Procodazole is a non-specific immunoprotective agent against viral and bacterial infections used with the compositions claimed herein. It is effective with one or more (5-aryl-1,2,4-thiadiazol)-3-yl thiourea derivatives or (5-aryl-1,2,4-thiadizol)-3-yl urea derivatives in treating viral infections and can be combined with one or more other therapeutic agents.

The combination therapy can be sequential, that is the treatment with one agent first and then the second agent, or it can be treatment with both agents at the same time. The sequential therapy can be within a reasonable time after the completion of the first therapy before beginning the second therapy. The treatment with both agents at the same time is preferred and can be in the same daily dose or in separate doses. For example treatment with one agent on day 1 and the other on day 2. The exact regimen will depend on the disease being treated, the severity of the infection and the response to the treatment.

2. Unit Dosage

The compounds of the present invention may be administered in a unit dosage form and may be prepared by any methods well known in the art. Such methods include combining the compounds of the present invention with a carrier or diluent which constitutes one or more accessory ingredients. Typically, the formulations are prepared by uniformly mixing the active ingredient with liquid carriers or finely divided solid carriers or both, and then if necessary shaping the product. A pharmaceutical carrier is selected on the basis of the chosen route of administration and standard pharmaceutical practice. Each carrier must be "acceptable" In the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Dosage forms (compositions suitable for administration) comprise from about 1 milligram to about 1000 milligrams of active ingredients per dosage unit. Preferably the dosage forms will contain from about 10 mg to about 500 mg. In these pharmaceutical compositions the active ingredient will ordinarily be present in an amount of about 0.5 to about 95% by weight based on the total weight of the dosage unit.

3. Pharmaceutical Kits

The present invention also includes pharmaceutical kits useful, for example, for the treatment of hepatitis infection, which comprise one or more containers containing a pharmaceutical composition comprising a therapeutically effective amount of a (5-aryl-1,2,4-thiadiazol)-3-yl thiourea derivatives or (5-aryl-1,2,4-thiadizol)-3-yl urea derivatives, and ribavirin or suitable interferon or a combination of ribavirin and an interferon. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit. In the present disclosure it should be understood that the specified materials and conditions are important in practicing the invention but that unspecified materials and conditions are not excluded so long as they do not prevent the benefits of the invention from being realized.

Specific examples of pharmaceutical acceptable carriers and excipients that may be used to formulate oral dosage forms of the present invention are described in U.S. Pat. No. 3,903,297 to Robert, issued Sep. 2, 1975.

Techniques and compositions for making dosage forms useful in the present invention are described herein below.

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary or paste.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin and cyclodextrin derivatives and the like.

Capsule or tablets can be easily formulated and can be made easy to swallow or chew. Tablets may contain suitable binders, lubricants, diluents, disintegrating agents, coloring agents, flavoring agents, flow-inducing agents, and melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethlcellose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. Molded tablets may be made by molding in a suitable machine a mixture of the powdered active ingredient moistened with an inert liquid diluent.

The tablets may optionally be coated or scored and may be formulated so as to provide slow or controlled release of the active ingredient. Tablets may also optionally be provided with an enteric coating to provide release in parts of the gut other than the stomach.

Formulations suitable for topical administration in the mouth wherein the active ingredient is dissolved or suspended in a suitable carrier include lozenges which may comprise the active ingredient in a flavored carrier, usually sucrose and acacia or tragacanth; gelatin, glycerin, or sucrose and acacia; and mouthwashes comprising the active ingredient in a suitable liquid carrier.

Topical applications for administration according to the method of the present invention include ointments, cream, suspensions, lotions, powder, solutions, pastes, gels, spray, aerosol or oil. Alternately, a formulation may comprise a transdermal patch or dressing such as a bandage impregnated with an active ingredient and optionally one or more carriers or diluents. To be administered in the form of a transdermal delivery system, the dosage administration will, of course, be continuous rather than intermittent throughout the dosage regimen.

The topical formulations may desirably include a compound which enhances absorption or penetration of the active ingredient through the skin or other affected areas. Examples of such dermal penetration enhancers include dimethylsulfoxide and related analogues.

The oil phase of the emulsions of the composition used to treat subjects in the present invention may be constituted from known ingredients in a known manner. This phase may comprise one or more emulsifiers. For example, the oily phase comprises at least one emulsifier with a fat or an oil or with both a fat and an oil or a hydrophilic emulsifier is included together with a lipophilic emulsifier which acts as a stabilizer. Together, the emulsifier(s) with or without stabilizer(s) make up an emulsifying was, and the wax together with the oil and/or fat make up the emulsifying ointment base which forms the oily dispersed phase of the cream formulations.

Emulsifiers and emulsion stabilizers suitable for use in the formulation include Tween 60, Span 80, cetosteryl alcohol, myristyl alcohol, glyceryl monostearate and sodium lauryl sulphate, paraffin, straight or branched chain, mono-or dibasic alkyl esters, mineral oil. The choice of suitable oils or fats for the formulation is based on achieving the desired cosmetic properties, the properties required and compatibility with the active ingredient.

The compounds may also be administered vaginally for example, as pessaries, tampons, creams, gels, pastes, foams or spray formulations containing in addition to the active ingredient. Such carriers are known in the art.

Formulations for rectal administration may be presented as a suppository with a suitable base comprising, for example, cocoa butter or a salicylate.

Formulations suitable for nasal administration may be administered in a liquid form, for example, nasal spray, nasal drops, or by aerosol administration by nebulizer, including aqueous or oily solutions of the active ingredient. Formulations for nasal administration, wherein the carrier is a solid, include a coarse powder having a particle size, for example, of less than about 100 microns, preferably less than about 50 microns, which is administered in the manner in which snuff is taken, i.e., by rapid inhalation through the nasal passage from a container of the powder held close up to the nose.

Formulations suitable for parenteral administration include aqueous and non-aqueous isotonic with the blood of the intended recipient; and aqueous and non-aqueous sterile suspensions which may include suspending systems which are designed to target the compound to blood components or one or more organs. The formulations may be presented in unit-dose or multi-dose sealed containers, for example, ampoules and vials. Extemporaneous injections solutions and suspensions may be prepared from sterile powders, granules and tablets of the kind previously described.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

Intravenously, the most preferred doses can range from about 1 to about 10 mg/kg/minute during a constant rate infusion. (5-Aryl-1,2,4-thiadizol)-3-yl derivatives or (5-aryl-1,2,4-thiadizol)-3-yl urea derivatives in combination with interferon and/or ribavirin can be administered in a single daily dose, or the total daily dosage can be administered in divided doses of two, three, or four times daily. The (5-aryl-1,2,4-thiadizol)-3-yl- derivatives or (5-aryl-1,2,4-thiadizol)-3-yl urea derivatives along with interferon and/or ribavirin can be given in one or more doses on a daily basis or from one to three times a week.

The present invention additionally include administering compounds of the herein described formula for the use in the form of veterinary formulations, which may be prepared, for example, by methods that are conventional in the art.

Useful pharmaceutical dosage forms for administration of the compounds of this invention are illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings can be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Liposomes can also be used for injectable compositions.

Suspension

An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

F. METHOD OF TREATMENT

The method of treatment can be any suitable method which is effective in the treatment of the particular virus or viral infection that is being treated. Treatment includes administering a therapeutically effective amount of the compounds of the present invention in a form described herein above, to a subject in need of treatment. As previously described, the composition can be administered oral, rectal, topical, vaginally, nasally, parenterally, intravenously and the like. The method of applying an effective amount varies depending on the viral infection being treated and the desired blood level.

It is believed that parenteral treatment by intravenous, subcutaneous, or intramuscular application of (5-aryl-1,2,4-thiadiazol)-3-yl thiourea derivatives or (5-aryl-1,2,4-thiadizol)-3-yl urea derivatives, ribavirin and/or interferon, formulated with an appropriate carrier, additional viral inhibiting compound or compounds or diluent to facilitate application will be the preferred method of administering the compounds to mammals or warm blooded animals.

The interferon and/or ribavirin can be provided in their usual dosage form and amounts and administered separately.

G. TEST METHODS

Cell Preparation

Madin-Darby bovine kidney (MDBK) cells were passaged in T-75 flasks for use in the assay. On the day preceding the assay, the cells were trypsinized, pelleted, counted and resuspended at $6\times10^4$/well in tissue culture medium. Cells were added to 96 well flat bottom plates in a volume of 100 $\mu$l per well.

Virus Preparation

A pretitered aliquot of virus is removed from the freezer (−80° C.) and allowed to thaw slowly to room temperature in a biological safety cabinet. The virus is diluted into tissue culture medium such that the amount of virus added to each well in a volume of 100 $\mu$l will be the amount determined to give complete cell killing at 6 days post-infection.

Compound Preparation (5-Phenyl-1,2,4-thiadiazol)-3-yl thiourea and ribavirin (purchased from Sigma) were dissolved in DMSO as a stock solution. Interferon was purchased from PBL Biomedical Laboratories (New Brunswick, N.J.) and was in PBS solutions. On the day of testing, the drug stock is diluted in the medium to the desired high concentration and then further diluted in the medium in half log series.

Addition of Virus and the Tested Compounds

The day following plating of cells, plates are removed from the incubator, and medium is removed and discarded. Drug dilutions are added to appropriate wells of the microtiter plate in a volume of 100 $\mu$l per well. Each dilution is set up in triplicate. Complete medium or complete medium containing appropriately diluted virus is added to appropriate wells in a volume of 100 $\mu$l per well.

Plate Format

The format of the test plate has been standardized. Each plate contains cell control wells (cell only), virus control wells (cells plus virus), drug toxicity control wells (cells plus drug only), drug colorimetric control wells (drug only) as well as experimental wells (drugs plus cells plus virus).

XTT Assay

The cell viability was evaluated by a dye (XTT) uptake procedure. XTT-tetraolium is metabolized by the mitochontrial enzymes of metabolically active cells to a soluble formazan product, allowing the rapid quantitative analysis of the inhibition of virus-induced cell killing by antiviral test substances.

XTT solution was prepared daily as a stock of 1 mg/ml in PBS. Phenazine methosulfate (PMS) solution was prepared at 15 mg/ml in PVBS and stored in the dark at −20° C. STT/PMS stock was prepared immediately before use by diluting PMS 1:100 into PBS and adding 40 $\mu$l per ml of XTT solution. Fifty microliters of XTT/PMS was added to each well of the plate (each well had been loaded with 100 μl fresh medium) and the plate was reincubated for 4 hours at 37° C.

Adhesive plate sealers were used in place of the lids, the sealed plate was inverted several times to mix the soluble formazan product and the plate was read spectrophotometrically at 450 nm (XTT) with a Molecular Devices Vmax plate reader.

Data Analysis

The efficacy and toxicity of inteferons are analyzed using a computer program (developed by Southern Research Institute) which calculates % CPE reduction, % cell viability, $IC_{25,50\ \&\ 95}$, $TC_{5,50\ \&\ 95}$ and other indices.

Combination effects are analyzed statistically by Prichard and Shipman method. Effects of the drug combination on efficacy and toxicity are calculated based on the activity or toxicity of the two compounds when tested alone. The expected additive inhibition rate of virus production or the expected additive cell viability rate subtracted from the experimentally determined inhibition rate or viability rate at each combination concentration results in a positive value (synergy), a negative value (antagonism), or zero (addivity).

H. EVALUATION OF HUMAN α-INTERFERON FOR ACTIVITY AGAINST BVDV IN VITRO

Interferon α is a family of related, homologous proteins, each exhibiting a unique activity profile. The activities of the different α interferon species on viruses can vary twenty fold or more. To identify the ideal α interferon for the following combination studies in the BVDV system, all 12 human IFN-α species were tested. Universal Type I Interferon was also used. It crosses the species barrier and can be used as a substitute for any mammalian Type I Interferon.

The results are summarized below:

| INF-αA | $IC_{50}$ U/ml | $TC_{50}$ U/ml | TI | Comments |
|---|---|---|---|---|
| A | 2.54 | >316.00 | >124.22 | Active/Nontoxic |
| B2 | 37.40 | >316.00 | >8.45 | Active/Nontoxic |
| C | 9.12 | >316.00 | >34.66 | Active/Nontoxic |
| D | 11.60 | >316.00 | >27.31 | Active/Nontoxic |
| F | 33.00 | >316.00 | >9.57 | Active/Nontoxic |
| G | 23.60 | >316.00 | >13.40 | Active/Nontoxic |
| H2 | 7.00 | >316.00 | >45.12 | Active/Nontoxic |
| I | 26.80 | >316.00 | >11.81 | Active/Nontoxic |
| J1 | 10.60 | >316.00 | >29.90 | Active/Nontoxic |
| K | 24.80 | >316.00 | >12.72 | Active/Nontoxic |
| WA | 6.75 | >316.00 | >46.78 | Active/Nontoxic |
| 4b | 6.08 | >316.00 | >51.97 | Active/Nontoxic |
| Universal | 9.26 | >316.00 | >34.13 | Active/Nontoxic |
| Ribavirin | 0.66* | 7.19* | 10.82 | Active/Toxic |

*The unit is μg/ml

Ribavirin and INF-α are used clinically as a combination therapy for Hepatitis C infected patients because such therapy increases a sustained response rate, in comparison to INF-α monotherapy. However, it is unknown whether such synergistic combination effect can be observed in the BVDV in vitro infection system. To address the issue, a combination study of ribavirin and INF-αA was tested. The results are presented below.

Antiviral Percentage Inhibition

| Ribavirin concentration | INF-αA Concentration 0 | 0.06 | 0.19 | 0.601 | 1.899 | 6 |
|---|---|---|---|---|---|---|
| 7.500 | 41.6 | 19.5 | 36.1 | 18 | 29.5 | 21.2 |
| 2.373 | 31.5 | 33.9 | 51.4 | 66 | 94.6 | 82.4 |
| 0.751 | 3 | 4.5 | 17.1 | 40.9 | 47.4 | 76.8 |
| 0.238 | 5 | 3.2 | 1.1 | 32.9 | 18.1 | 64.1 |
| 0.075 | 0 | 0 | 0 | 4.8 | 5.6 | 57.3 |
| 0 | 0 | 0 | 0 | 0 | 5.8 | 15.3 |

The antiviral synergy at 95% confidence is 134 with an antagonism value of −39.

Cytotoxicity Percentage

| Ribavirin concentration | INF-αA Concentration 0 | 0.06 | 0.19 | 0.601 | 1.899 | 6 |
|---|---|---|---|---|---|---|
| 7.500 | 54.2 | 59.7 | 68 | 61.5 | 52.4 | 69.6 |
| 2.373 | 10.8 | 20.2 | 21.8 | 16 | 10 | 25.7 |
| 0.751 | 0 | 11 | 0 | 1.8 | 0 | 7.7 |
| 0.238 | 0.6 | 6.1 | 0 | 0 | 0 | 12.9 |
| 0.075 | 0 | 0 | 0 | 6.9 | 4 | 9.3 |
| 0 | 0 | 0 | 0 | 0 | 0 | 3.9 |

The cytotoxicity synergy at 99% confidence level is 0 and the antagonism is 0. A test of the combination Effect of Ribavirin and (5-Phenyl-1,2,4-thiadiazol)-3-yl thiourea provided the following results. The combination of ribavirin and (5-Phenyl-1,2,4-thiadiazol)-3-yl thiourea (compound) improves the toxicity of ribavirin towards BVDV cells.

Antiviral Percentage Inhibition

| Compound concentration | Ribavirin Concentration 0 | 0.075 | 0.238 | 0.751 | 2.373 | 7.5 |
|---|---|---|---|---|---|---|
| 2.00 | 29.5 | 29.5 | 33.2 | 33 | 35.1 | 60.3 |
| 0.633 | 7.6 | 7.6 | 12.4 | 12.2 | 14.9 | 48 |
| 0.200 | 3.6 | 3.6 | 8.6 | 8.4 | 11.2 | 45.7 |
| 0.063 | 5 | 5 | 9.9 | 9.8 | 12.5 | 46.5 |
| 0.020 | 7.3 | 7.3 | 12.1 | 11.9 | 14.6 | 47.8 |
| 0 | 0 | 0 | 5.2 | 5 | 7.9 | 43.7 |

The antiviral synergy at 95% confidence level is 27 with an antagonism of −6.

Cytotoxicity Percentage

| Compound concentration | Ribavirin Concentration 0 | 0.075 | 0.238 | 0.751 | 2.373 | 7.5 |
|---|---|---|---|---|---|---|
| 2.00 | 18.8 | 29.8 | 22.1 | 15.6 | 15.1 | 26.2 |
| 0.633 | 16.9 | 6.7 | 10.2 | 15.1 | 10.5 | 20.2 |
| 0.200 | 6.2 | 1.1 | 6.7 | 4.6 | 9.3 | 23.6 |
| 0.063 | 6.7 | −1.3 | 5.2 | 2.2 | 12.4 | 34.8 |
| 0.020 | 16.3 | 0.8 | 1.3 | −2.9 | 2.4 | 49.6 |
| 0 | 0 | −15.1 | −8.6 | −12.3 | 27.2 | 46.7 |

The cytotoxicity synergy at 95% confidence level is of 35 with a −233 antagonism.

| Antiviral Percentage Inhibition | | | | | | |
|---|---|---|---|---|---|---|
| | INF-αA Concentration | | | | | |
| Compound concentration | 0 | 0.06 | 0.19 | 0.601 | 1.899 | 6 |
| 2.00 | 25.9 | 28.8 | 27.9 | 57.1 | 63.3 | 66.9 |
| 0.633 | 11.7 | 12.2 | 10.1 | 12.8 | 32.2 | 38.4 |
| 0.200 | 4 | 12.9 | 3.4 | 1.3 | 7.8 | 28.9 |
| 0.063 | 7 | 6.8 | 0.6 | 2.1 | 7.4 | 16.1 |
| 0.020 | 5.8 | 0.8 | 0 | 0 | 12.7 | 12.6 |
| 0 | 0 | 3.1 | 0 | 0 | 6.3 | 11.2 |

The antiviral synergy at 95% confidence is 90 with an antagonism of −12.

| Cytotoxicity Percentage | | | | | | |
|---|---|---|---|---|---|---|
| | INF-αA Concentration | | | | | |
| Compound thioreau | 0 | 0.06 | 0.19 | 0.601 | 1.899 | 6 |
| 2.00 | 10.3 | 23.7 | 17.1 | 6.6 | 4.4 | 15.8 |
| 0.633 | 13.5 | 25.2 | 21.2 | 0.1 | 11.7 | 9.4 |
| 0.200 | 8.3 | 7.1 | 15.3 | 0.9 | 0 | 12 |
| 0.063 | 5.8 | 13.5 | 14.9 | 0 | 0 | 13.7 |
| 0.020 | 0 | 0 | 8.7 | 0 | 0 | 49.6 |
| 0 | 0 | 0 | 0 | 0 | 0 | 0 |

The cytotoxicity synergy plot at 95% confidence is 5 with an antagonism of −5.

The Tests Show

Ribavirin and INF-αA act synergistically against BVDV in vitro (5-Phenyl-1,2,4-thiadiazol)-3-yl thiourea does not have antagonistic effect on activity of ribavirin against BVDV in vitro, but it imposes antagonistic effect on toxicity of ribavirin towards the testing of the cells in vitro, and (5-Phenyl -1,2,4-thiadiazol)-3-yl thiourea acts synergistically with INF-αA against BVDV in vitro.

What is claimed is:

1. A method of treating a viral infection comprising administering to a patient in need thereof a therapeutically effective amount of a combination of:

(a.) a (5-aryl-1,2,4-thiadiazol)-3-yl thiourea derivative or a (5-aryl-1,2,4-thiadiazol)-3-yl urea derivative having the formula:

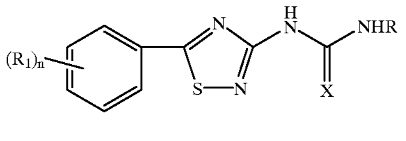

wherein X is oxygen or sulfur; R is hydrogen or alkyl having from 1–3 carbons; n is 0–4;

and $R_1$ is independently selected from the group consisting of hydrogen, alkyl having from 1 to 7 carbon atoms, chloro, bromo, fluoro, oxychloro, and alkoxy having the formula $—O(CH_2)_yCH_3$ wherein y is from 1 to 6; or a pharmaceutical addition salt or a prodrug thereof; and (b.) ribavirin or interferon or combination of ribavirin and interferon.

2. A method according to claim 1 wherein said viral infection is hepatitis.

3. A method according to claim 2 wherein said viral infection is hepatitis C or hepatitis B.

4. A method according to claim 2 wherein said (5-aryl-1,2,4-thiadiazol)-3-yl thiourea derivative or (5-aryl-1,2,4-thiadiazol)-3-yl urea derivative is (5-phenyl-1,2,4-thiadiazol)-3-yl thiourea or a pharmaceutical addition salt thereof or a prodrug thereof.

5. A method according to claim 1 wherein said method comprises administering to a patient in need thereof from about 1 mg/kg body weight to about 10,000 mg/kg body weight of said (5-aryl-1,2,4-thiadiazol)-3-yl thiourea derivative or (5-aryl-1,2,4-thiadiazol)-3-yl urea derivative.

6. A method according to claim 1 wherein said (5-aryl-1,2,4-thiadiazol)-3-yl thiourea derivative or (5-aryl-1,2,4-thiadiazol)-3-yl urea derivative is administered in a solid form and wherein said solid form includes a carrier selected from the group consisting of lactose, sucrose, gelatin and agar.

7. A method according to claim 6 wherein from about 10 mg/kg body weight to about 6000 mg/kg body weight of said (5-aryl-1,2,4-thiadiazol)-3-yl thiourea derivative or (5-aryl-1,2,4-thiadiazol)-3-yl urea derivative is administered.

8. A method according to claim 7 wherein said (5-aryl-1,2,4-thiadiazol)-3-yl thiourea derivative or (5-aryl-1,2,4-thiadiazol)-3-yl urea derivative is administered in a liquid form and wherein said liquid form is selected from the group consisting of an aqueous solution, an alcohol solution, an emulsion, a suspension, a suspension reconstituted from non-effervescent or effervescent preparations, and a suspension in pharmaceutically acceptable fats or oils.

9. A method of treating hepatitis comprising administering to a patient in need thereof:

(a) a therapeutically effective amount of a (5-aryl-1,2,4-thiadiazol)-3-yl thiourea having the formula:

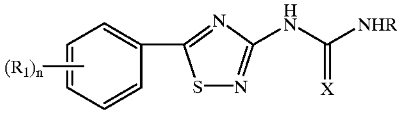

wherein X is sulfur, R is hydrogen, n is 0–4, and $R_1$ is independently selected from the group consisting of hydrogen or alkyl having from 1 to 7 carbon atoms; or a prodrug or a pharmaceutical addition salt thereof; and (b) a therapeutically effective amount of interferon or ribavirin or a combination thereof.

10. A method according to claim 9 wherein $R_1$ is hydrogen and n is 4.

11. A method according to claim 9 wherein from about 1 mg/kg body weight to about 6000 mg/kg body weight of said (5-aryl-1,2,4-thiadiazol)-3-yl thiourea derivative is administered.

12. A method according to claim 9 wherein said method further comprises administering an antiviral agent in a combination therapy, wherein said antiviral agent is selected from the group consisting of cyclovir, famciclovir, valacyclovir, ribavirin, beta globulin, and mixtures thereof.

13. A method of treating hepatitis C comprising administering to a patient in need thereof a therapeutically effective amount of a pharmaceutical composition comprising (5-phenyl-1,2,4-thiadiazol)-3-yl thiourea, or a pharmaceutical addition salt thereof, and a therapeutically effective amount of interferon-alpha.

14. A pharmaceutical composition comprising:

(a) a therapeutically effective amount of a (5-aryl-1,2,4-thiadiazol)-3-yl thiourea derivative or a (5-aryl-1,2,4-thiadiazol)-3-yl urea derivative having the formula:

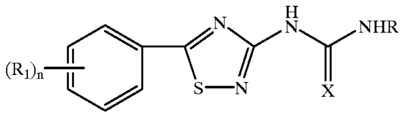

wherein X is oxygen or sulfur; R is hydrogen or alkyl having from 1–3 carbons; n is 0–4;

and $R_1$ is independently selected from the group consisting of hydrogen, alkyl having from 1 to 7 carbon atoms, chloro, bromo, fluoro, oxychloro, and alkoxy having the formula $—O(CH_3)_yCH_3$ wherein y is from 1 to 6; or a pharmaceutical addition salt or a prodrug thereof; and (b.) a therapeutically effective amount of ribavirin or interferon or a mixture thereof.

15. A pharmaceutical composition according to claim 14 comprising a pharmaceutically acceptable carrier and from about 1 mg to about 6000 mg of said (5-aryl-1,2,4-thiadiazol)-3-yl thiourea derivative or (5-aryl-1,2,4-thiadiazol)-3-yl urea derivative, or a pharmaceutical addition salt thereof.

16. A pharmaceutical composition according to claim 14 wherein said pharmaceutical addition salt is selected from the group consisting of chlorides, bromides, sulfates, nitrates, phosphates, sulfonates, formates, tartrates, maleates, malates, citrates, benzoates, salicylates, ascorbates, and mixtures thereof.

17. A pharmaceutical composition according to claim 14 comprising from about 150 mg to about 5000 mg of said (5-aryl-1,2,4-thiadiazol)-3-yl thiourea derivative or (5-aryl-1,2,4-thiadiazol)-3-yl urea derivative.

18. A pharmaceutical composition according to claim 14 wherein said composition further comprises a pharmaceutical carrier.

19. A pharmaceutical composition according to claim 18 where the carrier is in a solid form and the carrier is selected from the group consisting of lactose, sucrose gelatin and agar.

20. A pharmaceutical composition according to claim 18 where the carrier is in a liquid form and the liquid form is selected from the group consisting of an aqueous solution, an alcohol solution, an emulsion, a suspension, a suspension reconstituted from non-effervescent or effervescent preparations, and a suspension in pharmaceutically acceptable fats or oils.

21. A pharmaceutical composition according to claim 20 wherein said liquid form further comprises a member selected from the group consisting of a suspending agent, a diluent, a sweetener, a flavorant, a colorant, a preservative, an emulsifying agent, a coloring agent, and mixtures thereof.

22. A pharmaceutical composition according to claim 14 wherein said (5-aryl-1,2,4-thiadiazol)-3-yl thiourea derivative or (5-aryl-1,2,4-thiadiazol)-3-yl urea derivative has the formula:

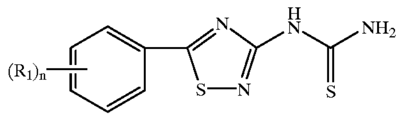

wherein n is 0–4 and $R_1$ is independently selected from the group consisting of hydrogen or alkyl having from 1 to 7 carbon atoms; or a prodrug or a pharmaceutical addition salt thereof.

23. A pharmaceutical composition according to claim 22 wherein $R_1$ is hydrogen and n is 4.

24. A pharmaceutical composition according to claim 14 comprising (5-phenyl-1,2,4-thiadiazol)-3-yl thiourea and interferon-alpha.

* * * * *

UNITED STATES PATENT AND TRADEMARK OFFICE

CERTIFICATE OF CORRECTION

PATENT NO. : 6,340,696 B1
DATED : January 22, 2002
INVENTOR(S) : James Berger Camden It is certified that error appears in the above-identified patent and that said Letters Patent is hereby corrected as shown below:

Column 18,
Line 3, insert -- , -- immediately after 'sucrose'.

Signed and Sealed this

Twenty-first Day of May, 2002

*Attest:*

JAMES E. ROGAN

*Attesting Officer* *Director of the United States Patent and Trademark Office*

UNITED STATES PATENT AND TRADEMARK OFFICE

CERTIFICATE OF CORRECTION

PATENT NO. : 6,340,696 B1 
DATED : January 22, 2002
INVENTOR(S) : Camden

It is certified that error appears in the above-identified patent and that said Letters Patent is hereby corrected as shown below:

Title page,
Item [*] Notice, delete the phrase “by 0 days” and insert -- by 14 days --

Signed and Sealed this

Twenty-first Day of September, 2004

JON W. DUDAS
*Director of the United States Patent and Trademark Office*